(12) United States Patent
Frankson et al.

(10) Patent No.: US 10,335,513 B2
(45) Date of Patent: Jul. 2, 2019

(54) HYDROPHILIZATION AND ANTIFOULING OF ENHANCED METAL SURFACES

(71) Applicant: Cardiac Pacemakers, Inc., St. Paul, MN (US)

(72) Inventors: Danielle Frankson, Dayton, MN (US); Joseph T. Delaney, Jr., Minneapolis, MN (US); Mary M. Byron, Roseville, MN (US); Adam McGraw, Mansfield, MA (US); David R. Wulfman, Minneapolis, MN (US); Kylee M. Lersch, Big Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/624,102

(22) Filed: Jun. 15, 2017

(65) Prior Publication Data
US 2017/0360987 A1    Dec. 21, 2017

Related U.S. Application Data

(60) Provisional application No. 62/350,764, filed on Jun. 16, 2016.

(51) Int. Cl.
| *A61L 27/34* | (2006.01) |
| *A61L 27/06* | (2006.01) |
| *A61L 27/04* | (2006.01) |
| *A61L 31/02* | (2006.01) |
| *A61L 31/10* | (2006.01) |
| *C09D 5/16* | (2006.01) |

(Continued)

(52) U.S. Cl.
CPC .............. *A61L 27/34* (2013.01); *A61L 27/04* (2013.01); *A61L 27/06* (2013.01); *A61L 31/022* (2013.01); *A61L 31/10* (2013.01); *C09D 5/1681* (2013.01); *C09D 123/06* (2013.01); *A61L 2400/18* (2013.01); *A61L 2420/02* (2013.01)

(58) Field of Classification Search
None
See application file for complete search history.

(56) References Cited

U.S. PATENT DOCUMENTS

| 4,179,337 A | 12/1979 | Davis et al. |
| 5,488,954 A | 2/1996 | Sleva et al. |
| 6,451,003 B1 | 9/2002 | Prosl et al. |

(Continued)

FOREIGN PATENT DOCUMENTS

| CN | 103079462 A | 5/2013 |
| EP | 0633031 A1 | 1/1995 |

(Continued)

OTHER PUBLICATIONS

Sigma Aldrich. https://www.sigmaaldrich.com/MSDS/MSDS/DisplayMSDSPage.do?country=US&language=en&productNumber=377996&brand=ALDRICH&PageToGoToURL=https%3A%2F%2Fwww.sigmaaldrich.com%2Fcatalog%2Fproduct%2Faldrich%2F377996%3Flang%3Den. Accessed May 21, 2018. 8 pp. (Year: 2018).*

(Continued)

*Primary Examiner* — Isaac Shomer
(74) *Attorney, Agent, or Firm* — Faegre Baker Daniels LLP (57) ABSTRACT

A coating for a roughened metal surface of an implantable medical device includes a poly(ethylene glycol) disposed on at least a portion of the roughened metal surface, wherein the poly(ethylene glycol) is covalently bonded directly to the roughened metal surface.

13 Claims, 4 Drawing Sheets

(51) Int. Cl.
*C09D 123/06* (2006.01)
*C08L 71/02* (2006.01)

(56) References Cited

U.S. PATENT DOCUMENTS

| | | | |
|---|---|---|---|
| 6,555,157 | B1 | 4/2003 | Hossainy |
| 6,617,027 | B2 | 9/2003 | Kim et al. |
| 6,669,980 | B2 | 12/2003 | Hansen |
| 6,793,960 | B1 | 9/2004 | Michal et al. |
| 7,037,332 | B2 | 5/2006 | Kutryk et al. |
| 7,322,965 | B2 | 1/2008 | Gibson et al. |
| 7,329,366 | B1 | 2/2008 | Gale et al. |
| 7,491,233 | B1 | 2/2009 | Ding et al. |
| 7,591,841 | B2 | 9/2009 | Hossainy et al. |
| 7,650,848 | B2 | 1/2010 | Brennan et al. |
| 8,131,376 | B1 | 3/2012 | Faraji et al. |
| 8,175,722 | B2 | 5/2012 | Parker et al. |
| 8,263,107 | B2 | 9/2012 | Pacetti et al. |
| 8,948,881 | B2 | 2/2015 | Fisk |
| 2001/0008931 | A1 | 7/2001 | Van Antwerp et al. |
| 2002/0019658 | A1 | 2/2002 | Munshi |
| 2003/0104028 | A1 | 6/2003 | Hossainy et al. |
| 2004/0044404 | A1 | 3/2004 | Stucke et al. |
| 2004/0167633 | A1* | 8/2004 | Wen .................. A61F 2/30767 623/23.57 |
| 2006/0004432 | A1 | 1/2006 | Parker et al. |
| 2006/0008500 | A1 | 1/2006 | Chavan et al. |
| 2006/0057180 | A1 | 3/2006 | Chilkoti et al. |
| 2007/0250045 | A1 | 10/2007 | Trieu |
| 2008/0140152 | A1 | 6/2008 | Imran et al. |
| 2008/0312356 | A1* | 12/2008 | Kobrin .................. A61L 27/34 523/113 |
| 2009/0043369 | A1 | 2/2009 | Radeloff |
| 2009/0093879 | A1 | 4/2009 | Wawro et al. |
| 2009/0123516 | A1 | 5/2009 | Agrawal et al. |
| 2010/0114225 | A1 | 5/2010 | Imran et al. |
| 2010/0152708 | A1 | 6/2010 | Li et al. |
| 2010/0198150 | A1 | 8/2010 | Michal et al. |
| 2011/0257702 | A1 | 10/2011 | Kara et al. |
| 2011/0306722 | A1 | 12/2011 | Lellouche et al. |
| 2013/0029421 | A1 | 1/2013 | Komvopoulos et al. |
| 2013/0098550 | A1 | 4/2013 | Sargeant et al. |
| 2014/0114435 | A1 | 4/2014 | Carpenter et al. |
| 2014/0172028 | A1 | 6/2014 | Meredith |
| 2014/0187666 | A1* | 7/2014 | Aizenberg .......... A61L 33/0094 523/113 |
| 2014/0316482 | A1 | 10/2014 | Kane et al. |
| 2015/0283301 | A1 | 10/2015 | Semetey et al. |
| 2016/0038743 | A1 | 2/2016 | Foster et al. |
| 2017/0173223 | A1 | 6/2017 | Delaney et al. |

FOREIGN PATENT DOCUMENTS

| | | |
|---|---|---|
| JP | 2002505930 A | 2/2002 |
| JP | 2005523116 A | 8/2005 |
| JP | 2010537728 A | 12/2010 |
| JP | 201363322 A | 4/2013 |
| WO | WO9307924 A1 | 4/1993 |
| WO | 1998017331 A1 | 4/1998 |
| WO | WO03072156 A1 | 9/2003 |
| WO | 2008006097 A2 | 1/2008 |
| WO | 2010001325 A2 | 1/2010 |
| WO | 2010057142 A2 | 5/2010 |
| WO | 2010094968 A2 | 8/2010 |
| WO | 2014041508 A1 | 3/2014 |
| WO | 2016025407 A1 | 2/2016 |

OTHER PUBLICATIONS

BE Yoldas. Hydrolysis of titanium alkoxide and effects of hydrolytic polycondensation parameters. Journal of Materials Science, vol. 21 1986, pp. 1087-1092. (Year: 1986).*

X Khoo, P Hamilton, GA O'Toole, BD Snyder, DJ Kenan, MW Grinstaff. "Directed Assembly of PEGylated-Peptide Coatings for Infection-Resistant Titanium Metal." Journal of the American Chemical Society, vol. 131, 2009, pp. 10992-10997. (Year: 2009).*

B Nie, T Long, H Li, X Wang, B Yue. "A comparative analysis of antibacterial properties and inflammatory responses for the KR-12 peptide on titanium and PEGylated titanium surfaces." RSC Advances, vol. 7, 2017, pp. 34321-34330. (Year: 2017).*

S Yamaguchi, et al. "Sonodynamic therapy using water-dispersed TiO2-polyethylene glycol compound on glioma cells: Comparison of cytotoxic mechanism with photodynamic therapy." Ultrasonics Sonochemistry, vol. 18, pp. 1197-1204. (Year: 2011).*

GD Venkatasubbu, S Ramasamy, V Ramakrishan, J Kumar. "Folate targeted PEGylated titanium dioxide nanoparticles as a nanocarrier for targeted paclitaxel drug delivery." Advanced Powder Technology, vol. 24, 2013, pp. 947-954. (Year: 2013).*

T Kotsokechagia, NM Zaki, K Syres, PD Leonardis, A Thomas, F Cellesi, N Tirelli. "PEGylation of Nanosubstrates (Titania) with Multifunctional Reagents: At the Crossroads between Nanoparticles and Nanocomposites." Langmuir, vol. 28, 2012, pp. 11490-11501. (Year: 2012).*

S Rahim, M Sasani Ghamsari, S Radiman. "Surface modification of titanium oxide nanocrystals with PEG." Scientia Iranica Transactions F: Nanotechnology, vol. 19(3), 2012, pp. 948-953. (Year: 2012).*

Barth, Andreas. "Review: The infrared Absorption of Amino Acide Side Chains," Progress in Biophysics & Molecular Biology, 74:141-173, 2000.

Grinstaff, Mark W and Meyers, Steven R. "Biocompatible and Bioactive Surface Modifications for Prolonged in Vivo Efficacy." Chem. Rev., 112(3):1-37, Mar. 14, 2012.

International Search Report and Written Opinion issued in PCT/US2017/046160, dated Oct. 20, 2017, 15 pages.

Park, Ki Dong; et. al. "Bacterial Adhesion on PEG Modified Polyurethane Surfaces." Biomaterials, 19:851-859, 1998.

Patel, Shyam; et. al. "Control of Cell Adhesion on Poly(methyl methacrylate)." Biomaterials, 27:2890-2897, 2006.

Xiao, Shou-Jun, et al. "Covalent Attachment of Cell-Adhesive, (Arg-Gly-Asp)-Containing Peptides to Titanium Surfaces." Langmuir 14:5507-5516, 1998.

Abdallah, H.I., et al., "Pacemaker contact sensitivity: clinical recognition and management", Ann Thorac Surg., 57 (4), Apr. 1994, pp. 1017-1018.

Au, Sam H., et al. "A New Angle on Pluronic Additives: Advancing Droplets and Understanding in Digital Microfluidics." Langmuir, 27:8586-8594, 2011.

Bain, Colin et al., "Formation of monolayer films by the spontaneous assembly of organic thiols from solution onto gold", J. Am. Chem. Soc., 111(1), 1989, pp. 321-335.

Benhabbour, Soumya et al., "Cell adhesion and proliferation on hydrophilic dendritically modified surfaces", Biomaterials, 29, (2008), pp. 4177-4186.

Berger, Manuel. "Biosensors Coated With Sulfated Polysaccharides for the Detection of Hepatocyte Growth Factor/ Scatter Factor in Cell Culture Medium." Biosensors and Bioelectronics, 26:1706-1709, 2010.

Ferringer, T., et al., "Telangiectatic erythematous cutaneous reaction to an implantable cardioverter defibrillator", Am J Contact Dermat., 14(1), (Mar. 2003), pp. 37-40.

Golda et al, "Oxygen plasma functionalization of parylene C coating for implants surface: Nanotopography and active sites for drug anchoring", Materials Science and Engineering C 33 (2013) 4221-4227.

Hamilton, Douglas W., et al. "Comparison of the Response of Cultured Osteoblasts and Osteoblasts Outgrown From Rat Calvarial Bone Chips to Nonfouling KRSR and FHRRIKA-Peptide Modified Rough Titanium Surfaces." Research Gate, Journal of Biomedical Materials Research Part B Applied Biomaterials, pp. 517-527, Nov. 2009.

Harder, P, et al., "Molecular Conformation in Oligo(ethylene glycol)-Terminated Self-Assembled Monolayers on Gold and Silver Surfaces Determines their Ability to Resist Protein Adsorption", J. Phys. Chem. B, 102, (1998), pp. 426-436.

Herrwerth, Sascha et al., "Factors that Determine the Protein Resistance of Oligoether Self-Assembled Monolayers—Internal (56) References Cited

OTHER PUBLICATIONS

Hydrophilicity, Terminal Hydrophilicity, and Lateral Packing Density", J. Am. Chem. Soc., 125, (2003), pp. 9359-9366.
Howard, Melissa, et al., "PEGylation of Nanocarrier Drug Delivery Systems: State of the Art", J. Biomed. Nanotechnol. 4, (2008), pp. 133-148.
International Preliminary Report on Patentability issued in PCT/US2015/044525, dated Feb. 23, 2017, 8 pages.
International Search Report and Written Opinion issued in PCT/US2015/015336, dated Jul. 10, 2015, 14 pages.
International Search Report and Written Opinion issued in PCT/US20151044525, dated Oct. 9, 2015, 10 pages.
International Search Report and Written Opinion issued in PCT/US2016/067409, dated Mar. 29, 2017, 14 pages.
Lin, Shaohui et al., "Antifouling Poly(Beta-Peptoid)s", Biomacromolecules, 12(7), (2011), pp. 2473-2582.
Ma, Hongwei et al., ""Non-Fouling" Oligo(ethylene glycol)-Functionalized Polymer Brushes Synthesized by Surface-Initiated Atom Transfer Radical Polymerization", Advanced Materials, 2004, 16(4), (Feb. 17, 2004), pp. 338-341.
Ma, Hongwei, et al., "Surface-Initiated Atom Transfer Radical Polymerizatino of Oligo9ethylene glycol) Methyl Methacrylate from a Mixed Self-Assembled Monolayer on Gold", Advanced Functional Materials, 16, (2006), pp. 640-648.
Maeda, Hatsuo, et al., "Electrochemical Coating with Poly(phenylene oxide) Films Bearing Oligoether Groups as a Tool for Elimination of Protein Adsorption to Electron Surfaces", Analytical Sciences, 15, (Jul. 1999), pp. 633-639.
Mrksich, Using Self-Assembled Monolayers to Understand the Interactions of Man-Made Surfaces with Proteins and Cells, Annual Reviews Blophys, Biomol, Struct. (1996) 25, pp. 55-78.
Needham, D., et al., Polymer-Grafted Liposomes: Physical Basis for the "Stealth" Property:, Journal of Liposome Research, 2(3), (1992), pp. 411-430.
Niebauer, M. J., et al., "Iridium oxide-coated defibrillation electrode: reduced shock polarization and improved defibrillation efficacy", Circulation, 96(10), (Nov. 18, 1997), pp. 3732-3736.
Olivares-Navarrete, Rene. "Osteoblasts Exhibit a More Differentiated Phenotype and Increased Bone Morphogenetic Protein Production on Titanium Alloy Substrates Than on Poly-Ether-Ether-Ketone." The Spine Journal, 12:265-272, 2012.
Orner, Brendan P. et al., "Arrays for the combinatorial Exploration of Cell Adhesion", J. Am. Chem. Soc., 126, (Aug. 14, 2004), pp. 10808-10809.
Pale-Grosdemange, Formation of Self-Assembled Monolayers by Chemisorption of Derivatives of Oligo(ethylene glycol) of Structure HS(CH2)11(OCH2CH2)mOH on Gold, Journal of American Chemical Society, vol. 113, No. 1, (1991), pp. 12-20.
Pensa, Evangelina et al., "The Chemistry of the SulfurGold Interface: In Search of a Unified Model", Accounts of Chemical Research, 45(8), (2012), pp. 1183-1192.
Reddy, Shravanthi T., et al. "Micropatterned Surfaces for Reducing the Risk of Catheter-Associated Urinary Tract Infection: An In Vitro Study on the Effect of Sharklet Micropatterned Surfaces to Inhibit Bacterial Colonization and Migration of Uropathogenic *Escherichia coli*." Journal of Endourology, 25(9):1547-1552, Sep. 2011.
Scardino, Andrew J. "Mini Review: Biomimetic Models and Bioinspired for Fouling Control," Biofouling, 27(1):73-86, Jan. 2011.
Schwartz, Zvi, et al. "RGD-Containing Peptide GCRGYGRGDSPG Reduces Enhancement of Osteoblast Differentiation by Poly(L-Lysine)-Graft-Poly(ethylene glycol)-Coated Titanium Surfaces." ResearchGate, Journal of Biomedical Materials Research Part A, pp. 458-472, Mar. 2004.
Singh, Nripen et al., "The role of independently variable grafting density and layer thickness of polymer nanolayers on peptide adsorption and cell adhesion", Biomaterials, 28, (2007), pp. 763-771.

Skoet, R. et al., "Epoxy Contact Dermititis due to Pacemaker Compounds", Cardiology, 99, (2003), 112.
Stouffer, Jan M. et al., "Polymer monolayers prepared by the spontaneous adsorption of sulfur-functionalized polystyrene on gold surfaces", Macromolecules, 21(5), (1988), pp. 1204-1208.
Su, Chiao-Tzu, et al. "A Facile Approach Toward Protein-Resistant Biointerfaces Based on Photodefinabie Poly-P-Xylylene Coating." Colloids and Surfaces B: Biointerfaces, 116:727-733, 2014.
Syburra, T. et al., "Gold-coated pacemaker implantation after allergic reactions to pacemaker compounds", Europace, 12(5), (May 2010), pp. 749-750.
Takae, Seiji et al., "Ligand density effect on biorecognition by PEGylated gold nanoparticles: regulated interaction of RCA 120 lectin with lactose installed to the distal end of tethered PEG strands on gold surface", Biomacromolecules, 6 (2), (2005), pp. 818-824.
Tan et al., Surface Engineering and Patterning Using Parylene for Biological Applications, Materials 2010, 3, 1803-1832; doi: 10.3390/ma3031803; ISSN 1996-1944, www.mdpi.com/journal/materials.
Terrill, Roger H. et al., "Structural Evolution of Hexadecanethiol Monolayers on Gold during Assembly: Substrate and Concentration Dependence of Monolayer Structure and Crystallinity", Langmuir, 14, (1998), pp. 845-654.
Tsai, Meng-Yu, et al. "Vapor-Based Multicomponent Coatings for Antifouling and Biofunctional Synergic Modifications." Adv. Funct. Mater., 24:2281-2287, 2014.
Vanderah, David J., et al. "Characterization of a Series of Self-Assembled Monolayers of Alkylated 1-Thiaologo (ethylene oxides) 4-8 on Gold." Langmuir 16:6527-6532, 2000.
Vanderah, David J., et al. "Self-Assembled Monolayers of Methyl 1-Thiahexa(ethylene oxide) for the Inhibition of Protein Adsorption." Langmuir 18:4674-4680, 2002.
Vanderah, David J., et al. "Synthesis and Characterization of Self-Assembled Monolayers of Alkylated 1-Thiahexa (ethylene oxide) Compounds on Gold." Langmuir 14:6919-6923, 1998.
Veiseh, Mandana et al., "Guided cell patterning on gold-silicon dioxide substrates by surface molecular engineering", Biomaterials, 25, (2004), pp. 3315-3324.
Vos, Johannes G. et al., "Formation and Characterization of Modified Surfaces", Supramolecular Assemblies, John Wiley & Sons, Ltd., (2003), pp. 87-152.
Zhu, B. et al., "Chain-length dependence of the protein and cell resistance of oligo(ethylene glycol)-terminated self-assembled monolayers on gold", J Biomed Mater Res., 56(3), (Sep. 5, 2001), pp. 406-416.
Buxadera-Palomero et al., "Antifouling coatings for dental implants: Polyethylene glycol-like coatings on titanium by plasma polymerization", Biointerphases, vol. 10, No. 2, Jun. 2015' pp. 029505-1 to 029505-11.
Harris et al., "*Staphylococcus aureus* adhesion to titanium oxide surfaces coated with non-functionalized and peptide-functionalized poly(l-lysine)-grafted-poly(ethylene glycol) copolymers", Biomaterials, vol. 25, No. 18, Aug. 2004, pp. 4135-4148.
Hyukjin Lee et al.; "Catechol-Grafted Poly(ethylene glycol) for PEGylation on Versatile Substrates", Languir, vol. 26, No. 6, Mar. 16, 2010, pp. 1 3790-3793.
International Search Report and Written Opinion issued in PCT/US2017/037697, dated Aug. 28, 2017, 13 pages.
Norma A. Alcantar et al., Polyethylene glycol-coated biocompatible surfaces:, Journal of Biomedical Materials Research, vol. 51, No. 3, Sep. 5, 2000, pp. 343-351.
Takao Hanawa, "A comprehensive review of techniques for biofunctionalization of titanium", Journal of Periodontal & Implant Science, vol. 41, No. 6, pp. 262-272, Jan. 2011.
International Preliminary Report on Patentability issued in PCT/US2016/067409, dated Jun. 28, 2018, 7 pages.

\* cited by examiner

HYDROPHILIZATION AND ANTIFOULING OF ENHANCED METAL SURFACES

CROSS-REFERENCE TO RELATED APPLICATION

This application claims priority to Provisional Application No. 62/350,764, filed Jun. 16, 2016, which is herein incorporated by reference in its entirety.

TECHNICAL FIELD

The present invention relates to preventing infections associated with implantable medical devices. More specifically, the invention relates to antifouling coatings and methods for forming antifouling coatings for implantable medical devices.

BACKGROUND

Implantable medical devices may include a housing and a lead or catheter for delivering therapy to a treatment site within a patient's body. For example, a pacemaker may include a housing, or pulse generator, containing electronics and a battery; and an electrical lead extending from the pulse generator to a treatment site—the heart. In another example, a drug delivery system may include a housing, or drug delivery pump, containing the pump, a battery, and a supply of the drug; and a catheter extending from the drug delivery pump to the treatment site requiring the drug. In some cases, the housing may be installed in a subcutaneous pocket within a patient's body.

Implanting a medical device within a patient inherently exposes the patient to a risk of a nosocomial (e.g., hospital-acquired) infection associated with bacteria adhering to the exterior of the medical device. For example, the average nosocomial infection rate associated with the implantation of pacemakers and implantable cardioverter defibrillators is approximately 3%. In some cases of infection, the implantable medical device, including a device housing and any associated electrical leads or catheters, must be completely removed. Following removal, the infection must be cured and the patient must heal enough to tolerate implantation of a replacement medical device. The costs of such infections are significant, not only intrinsically, but also in terms of the physical and emotional stress suffered by the patient.

Once implanted, the external surface of the medical device may also serve as an attachment point for red blood cells and platelets to coagulate. Should the coagulated red blood cells and platelet break off of the medical device and lodge within a blood vessel forming a blood clot, or thrombus. This thrombosis may restrict the flow through the blood vessel and endanger the patient.

What is needed is a way to prevent infections and thrombosis which may result from implanting a medical device within a patient.

SUMMARY

Example 1 is a coating for a roughened metal surface of an implantable medical device. The coating includes a poly(ethylene glycol) disposed on at least a portion of the roughened metal surface, wherein the poly(ethylene glycol) is covalently bonded directly to the roughened metal surface.

In Example 2, the coating of claim 1, wherein the poly(ethylene glycol) is covalently bonded directly to the roughened metal surface by an inorganic ether bond.

In Example 3, the coating of either of Examples 1-2, wherein the poly(ethylene glycol) covalently bonded directly to the roughened metal surface is a monolayer.

In Example 4, the coating of any of Examples 1-3, wherein an average molecular weight of the poly(ethylene glycol) is between about 200 grams per mole and about 20,000 grams per mole.

In Example 5, the coating of any of Examples 1-4, wherein an average molecular weight of the poly(ethylene glycol) is between about 400 grams per mole and about 4,000 grams per mole.

Example 6 is an implantable medical device including a roughened metal surface, and a coating according to any of Examples 1-5.

In Example 7, the implantable medical device of Example 6, wherein the roughened metal surface has an average surface roughness of about 0.20 micrometers or greater.

In Example 8, the implantable medical device of Example 6, wherein the roughened metal surface has an average surface roughness ranging from about 0.30 micrometers to about 30.0 micrometers.

In Example 9, the implantable medical device of any of Examples 6-8, wherein the roughened metal surface is a roughened titanium surface.

Example 10 is a method for coating a roughened metal surface of an implantable medical device. The method includes activating at least a portion of the roughened metal surface by forming hydroxyl groups on the surface, and treating the activated roughened metal surface with a poly(ethylene glycol) to covalently bond the poly(ethylene glycol) directly to the roughened metal surface.

In Example 11, the method of Example 10, wherein activating the roughened metal surface includes treating the surface with an oxygen-containing plasma.

In Example 12, the method of either of Examples 10 or 11, wherein the roughened metal surface is treated with the poly(ethylene glycol) within about 30 minutes of activating the roughened metal surface.

In Example 13, the method of any of Examples 10-12, wherein the poly(ethylene glycol) is covalently bonded directly to the roughened metal surface by an inorganic ether bond.

In Example 14, the method of any of Examples 10-13, wherein the poly(ethylene glycol) has an average molecular weight no greater than about 500.

In Example 15, the method of any of Examples 10-13, wherein the poly(ethylene glycol) has an average molecular weight greater than about 500, and the method further includes heating the roughened metal surface to a temperature between about 60° C. and about 200° C. after treating the activated roughened metal surface to melt away excess poly(ethylene glycol).

Example 16 is a coating for a roughened metal surface of an implantable medical device. The coating includes a poly(ethylene glycol) disposed on at least a portion of the roughened metal surface, wherein the poly(ethylene glycol) is covalently bonded directly to the roughened metal surface by an inorganic ether bond.

In Example 17, the coating of Example 16, wherein the poly(ethylene glycol) covalently bonded directly to the roughened metal surface is a monolayer.

In Example 18, the coating of either of Examples 16 or 17, wherein an average molecular weight of the poly(ethylene glycol) is between about 200 grams per mole and about 20,000 grams per mole.

In Example 19, the coating of any of Examples 16-18, wherein an average molecular weight of the poly(ethylene glycol) is between about 400 grams per mole and about 4,000 grams per mole.

Example 20 is an implantable medical device including a roughened metal surface, and a coating disposed on at least a portion of the roughened metal surface, the coating comprising a poly(ethylene glycol) disposed on at least a portion of the roughened metal surface, wherein the poly(ethylene glycol) is covalently bonded directly to the roughened metal surface by an inorganic ether bond.

In Example 21, the implantable medical device of Example 20, wherein the poly(ethylene glycol) covalently bonded directly to the roughened metal surface is a monolayer.

In Example 22, the implantable medical device of either of Examples 20 or 21, wherein an average molecular weight of the poly(ethylene glycol) is between about 200 grams per mole and about 20,000 grams per mole.

In Example 23, the implantable medical device of any of Examples 20-22, wherein an average molecular weight of the poly(ethylene glycol) is between about 400 grams per mole and about 4,000 grams per mole.

In Example 24, the implantable medical device of any of Examples 20-23, wherein the poly(ethylene glycol) is a hydroxy-terminated poly(ethylene glycol).

In Example 25, the implantable medical device of any of Examples 20-24, wherein the roughened metal surface has an average surface roughness of about 0.20 micrometers or greater.

In Example 26, the implantable medical device of any of Examples 20-25, wherein the roughened metal surface has an average surface roughness ranging from about 0.30 micrometers to about 30.0 micrometers.

In Example 27, the implantable medical device of any of Examples 20-26, wherein the roughened metal surface includes a metal oxide.

In Example 28, the implantable medical device of any of Examples 20-27, wherein the roughened metal surface is a roughened titanium surface.

In Example 29, the implantable medical device of any of Examples 20-28, wherein the roughened metal surface is an exterior surface of the implantable medical device.

Example 30 is a method for coating a roughened metal surface of an implantable medical device. The method includes activating at least a portion of the roughened metal surface by forming hydroxyl groups on the surface, and treating the activated roughened metal surface with a poly(ethylene glycol) to covalently bond the poly(ethylene glycol) directly to the roughened metal surface by an inorganic ether bond.

In Example 31, the method of Example 30, wherein activating the roughened metal surface of includes treating the surface with an oxygen-containing plasma.

In Example 32, the method of either of Examples 30 or 31, wherein the roughened metal surface is treated with the poly(ethylene glycol) within about 30 minutes of activating the roughened metal surface.

In Example 33, the method of any of Examples 30-32, wherein the poly(ethylene glycol) has an average molecular weight no greater than about 500.

In Example 34, the method of any of Examples 30-32, wherein the poly(ethylene glycol) has an average molecular weight greater than about 500, and the method further includes heating the roughened metal surface to a temperature between about 60° C. and about 200° C. after treating the activated roughened metal surface to melt away excess poly(ethylene glycol).

In Example 35, the method of any of Examples 30-34, wherein treating the activated roughened metal surface includes dipping the metal surface in liquid poly(ethylene glycol).

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Implantable medical devices often have exterior surfaces that are formed of one or more metals which may be enhanced by roughening for cosmetic and/or functional reasons. For example, in some cases, the metal surface may be roughened so that it is less likely to show fingerprints, or may be roughened, such as with a pattern, for identification purposes. The metal surface may also be roughened to enhance adhesion of a subsequently deposited layer on only a portion of the roughened metal surface. Roughening may be accomplished by, for example, treating the surface with a laser to melt the surface, by impacting the surface with glass beads or other media intended to dimple or scratch the surface, or by other mechanical means such as sanding or machining. In still other cases, the metal surface may be formed through the deposition of a metal coating on a metal or non-metal substrate by a process which may produce a rough surface, for example, sputter deposition.

While the roughening of these exterior metals surfaces is useful, bacteria generally preferentially adhere to rougher surfaces. Rougher surfaces can provide crevices or craters in which bacteria can adhere, shelter, and begin formation of colonies of bacteria which foul the surface of the implanted medical devices and may lead to an infection. Rougher surfaces may also be thrombogenic.

Embodiments of the disclosure form an immobilized monolayer of poly(ethylene glycol) linked by covalent bonds to a roughened metal surface of an implantable medical device. The resulting coating can render the roughened metal surface hydrophilic, anti-fouling, and/or anti-thrombogenic. The coating is also durable because it is covalently bonded directly to the roughened metal surface.

In some embodiments, a roughened metal surface can have an average surface roughness (Ra) of about 0.2 micrometers or greater. In some embodiments, the roughened metal surface can have surface roughness ranging from about 0.3 micrometers to about 3 micrometers, about 5 micrometers, about 10 micrometers, about 20 micrometers, or about 30 micrometers. Surface roughness measurements may be made with an optical surface profiler, such as a Zygo® NewView™ 6300 from the Zygo Corporation. Surface roughness averages are over a portion of the roughened metal surface. For example, where a surface includes a roughened portion and a non-roughened portion, the average surface roughness is determined over the roughened portion.

The geometry of the roughened metal surface may create such a hospitable surface for adhesion of bacteria and platelets that a hydrophilic coating may not be sufficient to reduce the adhesion. In some cases, the roughening process may create a different surface chemistry than that present before the roughening. For example, the roughing process may create a thicker layer of oxide passivation and/or a layer including other compounds, such as nitrides, which may interfere with formation of the coating. It has been found that embodiments of the immobilized monolayer of poly(ethylene glycol) linked by covalent bonds to the roughened metal surface are durable and effective in reducing bacterial adhesion.

Figure 1:
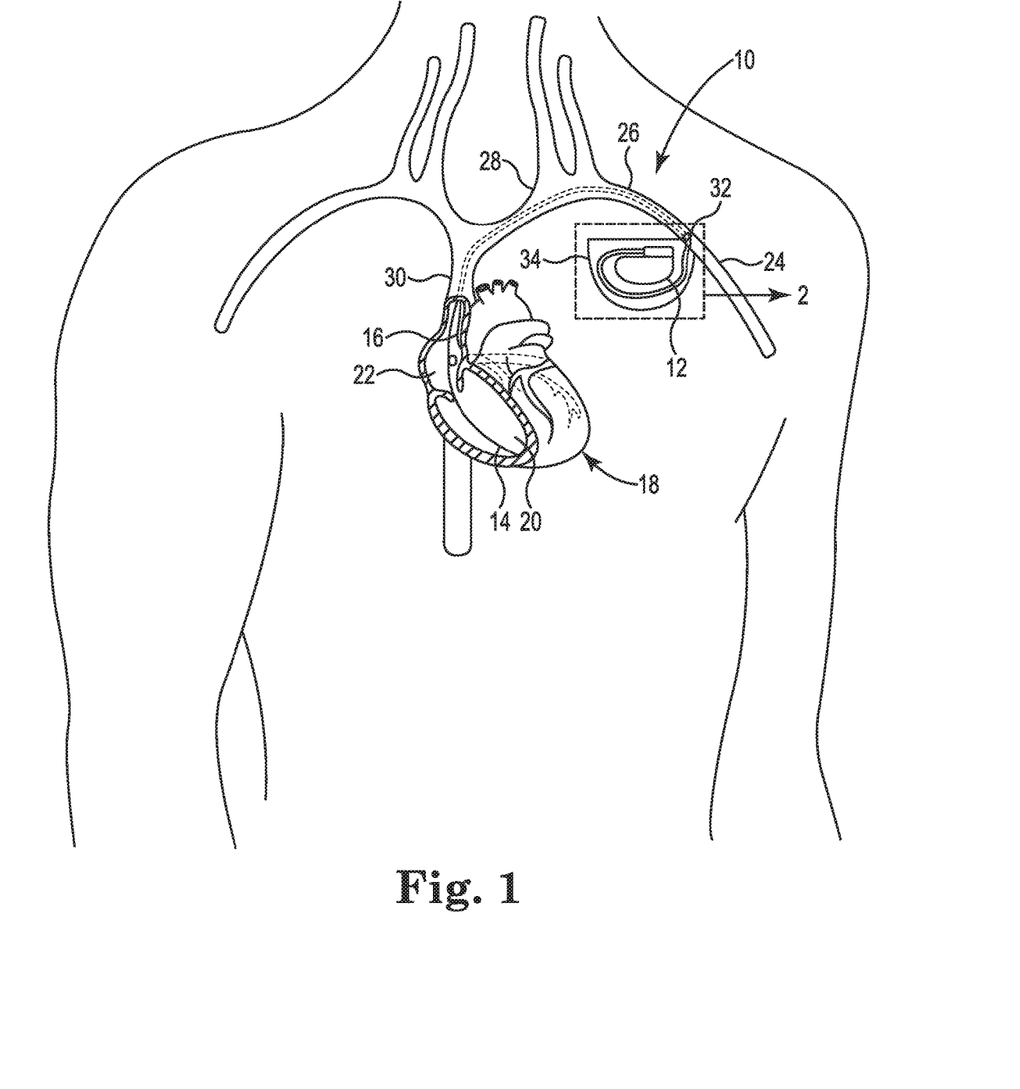
FIG. 1 is a schematic view of an implantable medical device subcutaneously implanted within a patient in accordance with embodiments of the disclosure.

FIG. 1 provides an illustrative but non-limiting example of an implantable medical device including a hydrophilic, anti-fouling, and anti-thrombogenic coating in accordance with the disclosure implanted into a subcutaneous pocket within a patient. The application and location are illustrative only, as implantable medical devices incorporating embodiments of the present invention may be used in a variety of anatomical locations and for a variety of additional purposes.

FIG. 1 illustrates an exemplary implantable medical device (IMD) 10 in the form of a cardiac rhythm management system. As shown in FIG. 1, the IMD 10 may include housing 12 and a plurality of leads 14, 16 connecting the housing 12 with treatment sites within a patient's heart 18. The housing 12 may be, for example, a pacemaker or pulse generator, and may include electronic circuitry (not shown) and a battery (not shown). The leads 14, 16 may include conductors and electrodes (not shown) as necessary to convey electrical pulses and signals between the housing 12 and the heart 18. As shown in FIG. 1, the heart 18 includes a right ventricle 20 and a right atrium 22. A major series of veins supplying blood to the heart 18 includes a left auxiliary vein 24, which flows into a left subclavian vein 26, which flows into a left brachiocephalic vein 28. The left brachiocephalic vein 28 flows into a superior vena cava 30, which supplies blood to the right atrium 22.

As further shown in FIG. 1, the plurality of leads 14, 16 may enter the vascular system through a vascular entry site 32. In some embodiments, the vascular entry site 32 may be formed in a wall of the left auxiliary vein 24. In other embodiments, the vascular entry site 32 may be formed in a wall of the left subclavian vein 26. The plurality of leads 14, 16 may extend from the left auxiliary vein 24, through the left subclavian vein 26, the left brachiocephalic vein 28, and the superior vena cava 30 to the heart 18. Within the heart 18, the lead 14 may be implanted in the right ventricle 20 and the lead 16 may be implanted in the right atrium 22. Thus, the right ventricle 20 and the right atrium 22 are treatment sites within the heart 18 that receive therapy from IMD 10 in the form of electrical pulses conveyed from the housing 12 by way of the leads 14, 16. In some embodiments, the housing 12 may require electrical grounding to tissue surrounding the subcutaneous pocket 34 to successfully provide therapy.

The housing 12 may be implanted in a subcutaneous pocket 34 in a patient's chest, as shown in FIG. 1 for example. A portion of the leads 14, 16 extending from the housing 12 to the vascular entry site 32 may also be located within the subcutaneous pocket 34. Any excess length of the leads 14, 16 may be coiled about the housing 12 within the subcutaneous pocket 34.

Although FIG. 1 illustrates the exemplary IMD 10 in the form of a subcutaneously-implanted pacemaker housing and lead system, the various embodiments can be implemented in any implantable medical device implanted in a patient. For example, embodiments may be employed with a subcutaneously-implanted implantable cardioverter-defibrillator (ICD) housing and lead system. Such a system may include a housing implanted in a subcutaneous pocket in a patient's chest, and a lead traversing a subcutaneous path from the subcutaneous pocket to the anterior precordial region. Embodiments may be employed within the subcutaneous pocket containing the ICD housing and along the subcutaneous path traversed by the lead. Other such implantable medical devices include, without limitation, cardioverter-defibrillator or cardiac resynchronization therapy devices, leadless pacing devices, endocardial leads, epicardial leads, neurostimulation systems such as spinal cord stimulation or deep brain stimulation device housings and associated leads, and implantable drug pumps, to name a few.

Figure 2:
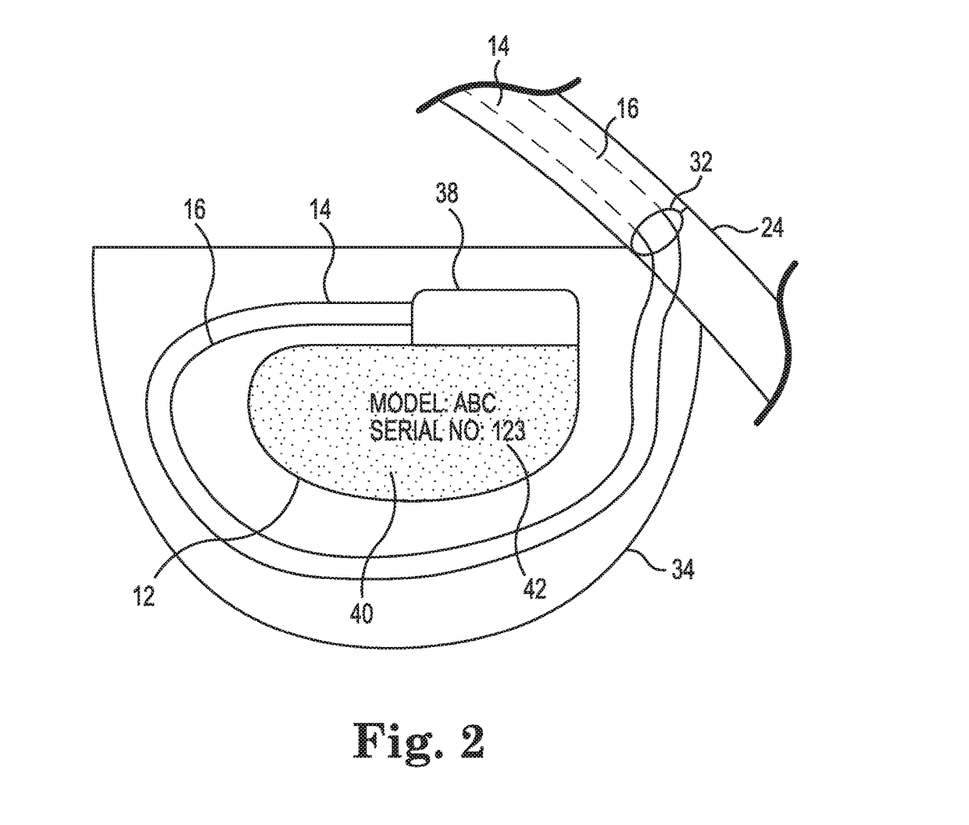
FIG. 2 is an enlarged schematic view of a portion of the implantable medical device of FIG. 1 including a poly(ethylene glycol) coating on a roughened metal surface in accordance with embodiments of the disclosure.

FIG. 2 is an enlarged schematic view of a portion of the implantable medical device of FIG. 1 including a hydrophilic, anti-fouling, and/or anti-thrombogenic coating in accordance with embodiments of the disclosure. As shown in FIG. 2, the IMD 10 may further include a header 38 for connecting the electrical leads 14, 16 to the housing 12. The housing 12 may include a roughened metal surface in the form of a media blasted surface 40. The media blasted surface 40 may be formed by the impact of media, such as glass beads, walnut shells, aluminum oxide particles, or silicon carbide particles driven against the surface by air or water. The housing 12 may also include a roughened metal surface in the form of a laser textured surface 42 which can be used to form a pattern for identification purposes. The media blasted surface 40 and the laser textured surface 42 may be coated with an immobilized monolayer of poly(ethylene glycol) linked by covalent bonds to the roughened metal surface, as described below. The coating may reduce infections and thrombosis by reducing bacteria growth and platelet adhesion on the surfaces it coats.

As noted above, in some embodiments, the IMD 10 may require electrical grounding between the housing 12 and tissue surrounding the subcutaneous pocket 34 to successfully provide therapy. A material or device covering a significant portion of the surface area of housing 12 may interfere with the electrical grounding of the IMD 10. In some embodiments, the poly(ethylene glycol) coating on the surface of the housing 12 is hydrophilic and electrically transparent. That is, the housing 12 may be electrically grounded to tissue surrounding the subcutaneous pocket 34 through the poly(ethylene glycol) coating.

Figure 3A:
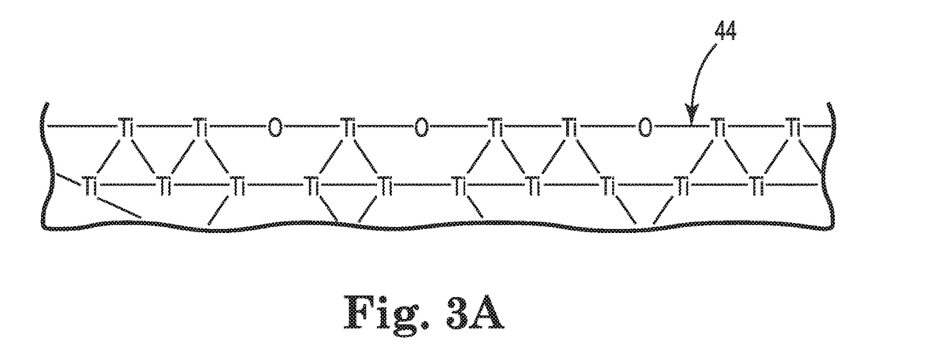
FIGS. 3A-3C are cross-sectional schematic diagrams illustrating the poly(ethylene glycol) coating covalently bonded directly to a roughened metal surface in accordance with embodiments of the disclosure.
Figure 3B:
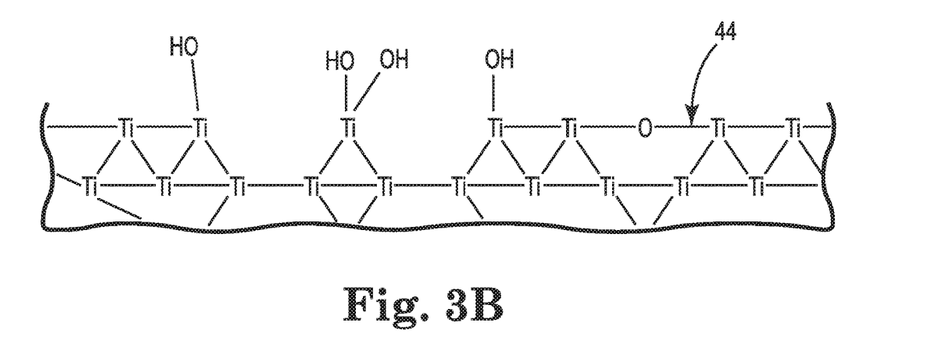
Figure 3C:
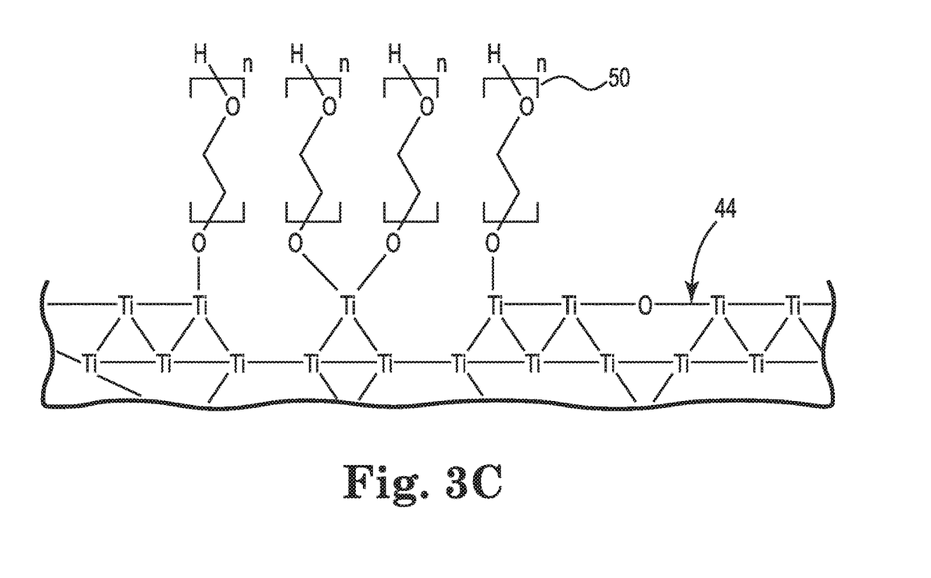

In some embodiments, the roughened metal surface can be activated, and then the activated surface can be treated directly with poly(ethylene glycol). The roughened surface can be activated by exposure to an oxygen-containing plasma, such as an oxygen plasma or a water plasma. FIGS. 3A-3C are cross-sectional schematic diagrams showing a process by which the poly(ethylene glycol) coating 50 can be covalently bonded directly to a roughened metal surface 44 in accordance with embodiments of the disclosure. The roughened metal surface 44 may be, for example, the media blasted surface 40 or the laser textured surface 42 of the IMD 10, described above. In the embodiment shown in FIGS. 3A-3C, the roughened metal surface 44 is a titanium metal surface. FIG. 3A shows cross-section of the roughened metal surface 44 prior to activation. In the illustrated embodiment, the roughened metal surface 44 includes a plurality of titanium-oxide bonds, as well as titanium-titanium bonds. FIG. 3B shows the roughened metal surface 44 following activation. As shown in FIG. 3B, at least some of the titanium-oxide bonds are cleaved by the oxygen-containing plasma, forming reactive hydroxyl groups on the roughened metal surface 44 when subsequently exposed to atmospheric moisture. In other embodiments, the oxygen-containing plasma may also include water, forming the reactive hydroxyl groups in situ. FIG. 3C shows the roughened metal surface 44 after it is treated with hydroxy-terminated poly(ethylene glycol) 50. As shown in FIG. 3C, the reactive hydroxyl groups on the roughened metal surface 44 form covalent inorganic ether bonds with the poly(ethylene glycol) 50. Inorganic ether bonds are those covalently bonding an organic molecule to an inorganic surface by an ether bond. Thus, as shown in FIG. 3C, the poly(ethylene glycol) 50 is covalently bonded directly to the roughened metal surface 44.

The hydroxyl groups formed during surface activation are in a high energy, highly reactive state and begin undesired reactions with other hydroxyl groups once the roughened metal surface 44 of the IMD 10 is removed from the oxygen-containing plasma. Reacted hydroxyl groups are unavailable to form covalent bonds during the treatment step. Thus, in some embodiments, the activated roughened metal surface 44 is treated with the poly(ethylene glycol) 50 within about 72 hours, within about 24 hours, within about 8 hours, within about 4 hour, within about 1 hour, within about 30 minutes, or within about 5 minutes of removal of the IMD 10 from the oxygen-containing plasma.

In some embodiments, the activated roughened metal surface 44 is treated directly with poly(ethylene glycol) 50 by dipping at least a portion of the roughened metal surface 44 in liquid poly(ethylene glycol) 50. In other embodiments, the activated roughened metal surface 44 may be treated by spraying the poly(ethylene glycol) 50 on to at least a portion of the roughened metal surface 44. Other suitable techniques may include inkjet printing, roll coating, screen printing, and microcontact printing the poly(ethylene glycol) 50 on to the activated roughened metal surface 44 on the IMD 10.

In some embodiments, the average molecular weight of the poly(ethylene glycol) 50 may be as low as about 200 g/mole, about 400 g/mole, about 1,000 g/mole, about 2,000 g/mole, or about 3,000 g/mole, or as high as, about 4,000 g/mole, about 8,000 g/mole, about 12,000 g/mole, about 16,000 g/mole, or about 20,000 g/mole, or an average molecular weight within any range defined between any pair of the foregoing values. In exemplary embodiments, the poly(ethylene glycol) 50 may have an average molecular weight from about 200 to 20,000 g/mole, about 400 to about 16,000 g/mole, about 1,000 to about 12,000 g/mole, about 2,000 to about 8,000 g/mole, or about 3,000 to about 4,000 g/mole. In some embodiments, the poly(ethylene glycol) 50 may have an average molecular weight of about 400 g/mole. In some other embodiments, the poly(ethylene glycol) 50 may have an average molecular weight of about 3,350 g/mole.

In some embodiments, the poly(ethylene glycol) 50 may have an average molecular weight low enough that the poly(ethylene glycol) 50 is a liquid at room temperature. For the purposes of this disclosure, room temperature is any temperature ranging from about 20° C. to about 25° C. In such embodiments, poly(ethylene glycol) 50 may have an average molecular weight no greater than about 500. For example, poly(ethylene glycol) 50 having an average molecular weight of about 400 g/mole is liquid at room temperature. In such embodiments, after the activated roughened metal surface 44 is treated with the poly(ethylene glycol) 50, excess poly(ethylene glycol) 50 may be allowed to drip off, leaving behind a monolayer of poly(ethylene glycol) 50 covalently bonded to the roughened metal surface 44 by an ether linkage, and some additional layers of poly(ethylene glycol) 50 attached to the monolayer by other than covalent bonds. While the additional layers of poly(ethylene glycol) 50 may not be durable, the poly(ethylene glycol) 50 monolayer is durable because it is linked to the roughened metal surface 44 by covalent bonds. The poly(ethylene glycol) 50 monolayer resists cracking or peeling from the roughened metal surface 44. The resulting coating provides a reliably hydrophilic, antifouling, and anti-thrombogenic exterior surface for the IMD 10.

In some other embodiments, the poly(ethylene glycol) 50 may have an average molecular weight high enough that at least some of the poly(ethylene glycol) 50 is in the form of a waxy solid that must be heated above room temperature to be in a liquid form. In such embodiments, the poly(ethylene glycol) 50 may have an average molecular weight greater than about 500 g/mole. In some embodiments, the poly(ethylene glycol) 50 may have an average molecular weight greater than about 1000 g/mole. In embodiments in which the poly(ethylene glycol) 50 must be heated above room temperature to be in a liquid form, the treated roughened metal surface 44 can be heated to melt away excess poly(ethylene glycol) 50. The melted excess poly(ethylene glycol) 50 is allowed to melt and drip off, leaving behind a monolayer of poly(ethylene glycol) 50 covalently bonded to the roughened metal surface 44 by an ether linkage, and some additional layers of poly(ethylene glycol) 50 attached to the monolayer by other than covalent bonds. In some embodiments, the treated roughened metal surface 44 can be heated to a temperature as low as about 60° C., about 80° C., about 100° C., or about 120° C., or as high as about 140° C., about 160° C., about 180° C., or about 200° C. to melt away excess poly(ethylene glycol) 50. In some embodiments, the treated metal surface 44 may be heated to a temperature between about 60° C. and about 200° C., about 80° C. and about 180° C., about 100° C. and about 160° C., and about 120° C. to about 140° C. In some embodiments, the treated roughened metal surface 44 can be heated to a temperature of about 130° C. to melt away excess poly(ethylene glycol) 50.

It is believed that poly(ethylene glycol) 50 having a higher average molecular weight (i.e., greater than about 500 g/mole) provides somewhat better anti-fouling than the lower average molecular weight poly(ethylene glycol) 50

(i.e. less than about 500 g/mole). Without wishing to be bound by any theory, it is believed that the higher average molecular weight poly(ethylene glycol) 50 provides a greater degree of steric hindrance to more effectively prevent bacteria from bonding to the surface. However, the poly(ethylene glycol) 50 having a lower average molecular weight is liquid at room temperature, and thus, is easier to work with and does not require a post-treatment heat to remove excess poly(ethylene glycol) 50.

Although the roughened metal surface 44 is shown as a titanium metal surface, other biocompatible metal surfaces which form a native oxide can also be used. Examples of other such metals can include stainless steel, iridium, and nitinol.

Figure 4:
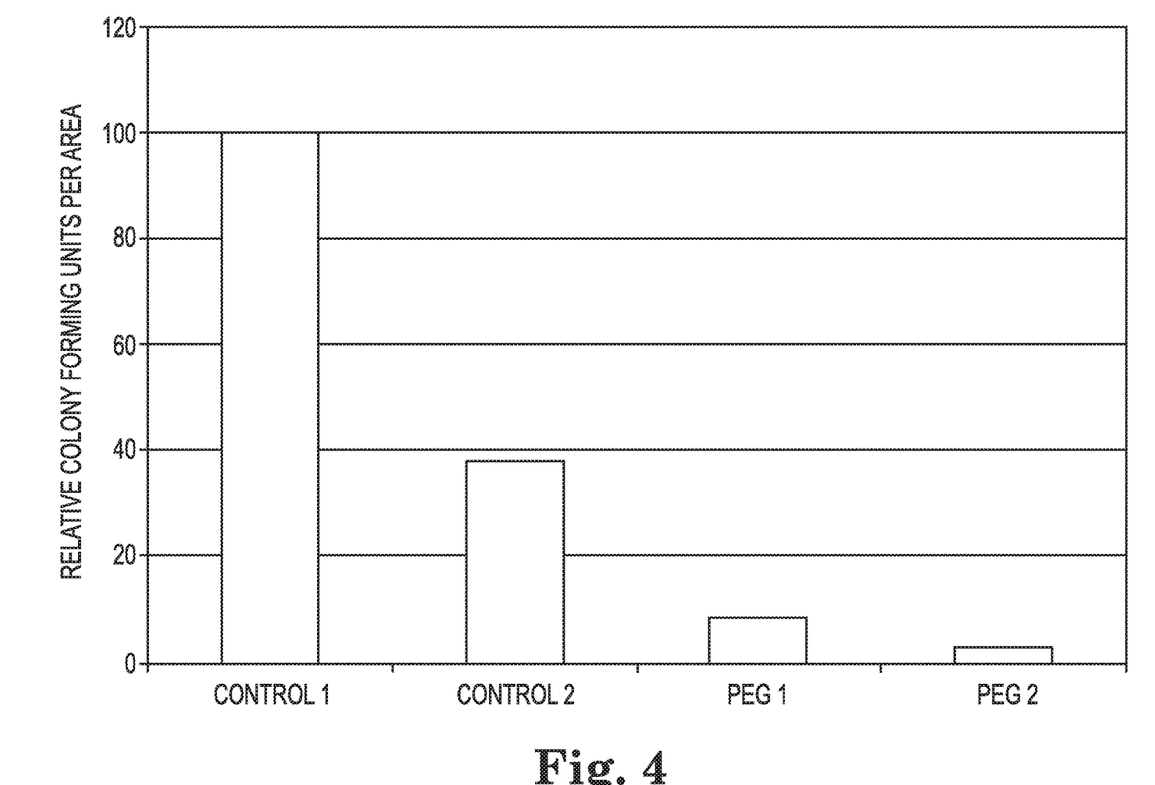
FIG. 4 is a graph of relative colony forming units over a predetermined area in accordance with embodiments of the disclosure.

The efficacy of an immobilized monolayer of poly(ethylene glycol) linked by covalent bonds to a roughened metal surface is shown in FIG. 4. FIG. 4 is a graph of relative colony forming units over a predetermined area on coated roughened metal surfaces in accordance with embodiments of the disclosure. Four samples of titanium coated with a sputter deposited titanium oxide layer ($TiO_2$) having a surface roughness (Ra) of about 0.2 micrometers were cleaned with isopropyl alcohol. Two of the four samples (designated PEG 1 and PEG 2) were activated with an oxygen plasma and treated with poly(ethylene glycol) having a molecular weight of about 3,350 grams/mole, as described above. The other two samples (designated Control 1 and Control 2) were neither activated nor treated with a poly(ethylene glycol). The four samples were subjected to a short term bacterial adhesion test. The samples were exposed to *S. aureus* for about 2 hours, then rinsed to remove bacteria that is not adhered to the roughened metal surface, fixed, stained, and placed in an agar plate. After about 12 hours at about 37° C., the number of colony forming units per area was determined for each sample.

The results are shown in FIG. 4, normalized for the Control 1. As shown in FIG. 4, both of the poly(ethylene glycol) samples showed significant and acceptable reductions in the quantity of bacteria adhered to the surface compared to the Control samples.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for coating a roughened titanium surface of an implantable medical device, the method comprising:
   providing a material with a roughened titanium metal surface;
   activating at least a portion of the roughened titanium surface with an oxygen containing plasma, wherein the activating step forms hydroxyl groups on the titanium surface; and
   treating the activated roughened titanium surface with a poly(ethylene glycol) to covalently bond the poly(ethylene glycol) directly to a titanium atom of the roughened titanium surface by an inorganic ether bond.

2. The method of claim 1, wherein the roughened metal surface is treated with the poly(ethylene glycol) within about 30 minutes of activating the roughened metal surface.

3. The method of claim 1, wherein the poly(ethylene glycol) has an average molecular weight no greater than about 500.

4. The method of claim 1, wherein the poly(ethylene glycol) has an average molecular weight greater than about 500, and the method further includes heating the roughened metal surface to a temperature between about 60° C. and about 200° C. after treating the activated roughened metal surface to melt away excess poly(ethylene glycol).

5. The method of claim 1, wherein treating the activated roughened metal surface includes dipping the metal surface in liquid poly(ethylene glycol).

6. The method of claim 1, wherein the poly(ethylene glycol) is hydroxy-terminated poly(ethylene glycol).

7. An implantable medical device made by the process of claim 1, the implantable medical device comprising a roughened titanium surface which is coated with a poly(ethylene glycol) coating, wherein the poly(ethylene glycol) is covalently bonded directly to a titanium atom of the roughened titanium surface by an inorganic ether bond.

8. The implantable medical device of claim 7, wherein the poly(ethylene glycol) covalently bonded directly to the roughened titanium metal surface is a monolayer.

9. The implantable medical device of claim 7, wherein an average molecular weight of the poly(ethylene glycol) is between about 200 grams per mole and about 20,000 grams per mole.

10. The implantable medical device of claim 7, wherein an average molecular weight of the poly(ethylene glycol) is between about 400 grams per mole and about 4,000 grams per mole.

11. The implantable medical device of claim 7, wherein the roughened titanium metal surface has an average surface roughness of about 0.20 micrometers or greater.

12. The implantable medical device of claim 7, wherein the roughened titanium metal surface has an average surface roughness ranging from about 0.30 micrometers to about 30.0 micrometers.

13. The implantable medical device of claim 7, wherein the roughened titanium metal surface is an exterior surface of the implantable medical device.

* * * * *